United States Patent [19]
Webber et al.

[11] Patent Number: 5,610,043
[45] Date of Patent: Mar. 11, 1997

[54] HUMAN PROSTATIC CELL LINES IMMORTALIZED BY ADENOVIRUS 12-SIMIAN VIRUS 40 (AD12/SV40) HYBRID VIRUS

[75] Inventors: Mukta M. Webber, Eagle, Mich.; Johng S. Rhim, Potomac, Md.

[73] Assignee: The United States of America as represented by the Department of Health and Human Services, Washington, D.C.

[21] Appl. No.: 234,981

[22] Filed: Apr. 28, 1994

[51] Int. Cl.$^6$ .............................. C12N 15/65; C12N 5/10
[52] U.S. Cl. ...................... 435/172.3; 435/366; 435/371
[58] Field of Search ........................... 435/240.2, 240.21, 435/122.3

[56] References Cited

PUBLICATIONS

M.S. Lee et al., Int. J. of Oncology, vol. 4:821–830 (1994).
Rhim et al., Cancer Research, vol. 50, 1990, pp. 5653s–5657s.
Rhim et al., Science, vol. 232, 1986, pp. 385–388.
Cussenot, O., et al., Journal of Urology 143, 881–886 (1991).
Kaighn, M E., et al, Cancer Research, 49, 3050–3056 (1989).
Kaur, P., et al., Journal of Virology 62, 1917 (1988).
Woodworth, C. D., et al., Cancer Research 48, 4620 (1988).
Peehl, D. M., et al. Prostate 10, 281 (1987).
Carter, B. S., et al., Cancer Research 50, 6830 (1990).
McNicol, J. P., et al., Journal of Urology 145, 850 (1991).
Anwar, K., et al., Cancer Research 52, 5991 (1992).
Gish, W. R., et al., J. Virol., 61:2864–2876 (1987).
Girardi, A. J., et al., J. Cell. Comp. Physiol. 65:69–84 (1965).
Gorman, C., et al., Science, 221:551–553 (1983).
Gallimore, P. H., et al., J. Mol. Biol. 89:49–72 (1974).
Schell, K., et al., Proc. Natl. Acad. Sci. USA, 55:81–88 (1966).
Stoner, G. D., et al., Cancer Res., 51:353–371 (1991).
Emami, S., et al., Proc. Natl. Acad. Sci. USA, 86:3194–3198 (1989).
Sommers, C. L., et al., Cancer Res., 52:5190–5197 (1992).
Molloy, C. J., et al., Exp. Mol. Pathol., 49:128–140 (1988).
Leong, A. S., et al., Histopathology, 13:435–442 (1988).
O'Guin, W.M., Schermer, A., Lynch, M. and Sun, T.: Differentiation–specific expression of keratin pairs. In: Cellular and Molecular Biology of Intermediate Filaments, R.D. Goldman and P.M. Steinert eds., New York, Plenum Press, pp. 301–334, 1990.
Sherwood, E. R., et al., Prostate, 18:303–314 (1991).
Truong, L. D., et al., Am. J. Clin. Pathol., Mar.:305–314 (1990).
Osborn, M., et al., Cell, 31:303–306 (1982).
Hendrix, M. J. C., et al., J. Natl. Cancer Inst., 84:165–174 (1992).
Lin, M.–F., et al., Cancer Res., 52:4600–4607 (1992).

Webber, M. M., In vitro models for Prostatic cancer: Summary. In: Models for prostate cancer G. P. Murphy (ed.) pp. 133–147, New York, NY: Alan R. Liss. (1980).
Webber, M. M., Growth and maintenance of normal prostatic epithelium in vitro—A human cell model. In: G. P. murphy, A. A. Sandberg and J. P. Karr (eds.), Models for Prostate Cancer, pp. 181–216,New York:Alan R.Liss. (1980).
Horoszewicz, J. S., et al., Cancer Res., 43:1809–1818 (1983).
Hasenson, M., et al., Prostate, 7:183–194 (1985).
de Launoit, Y., et al., Cancer Res., 51:5165–5170 (1991).
Simard, J., et al., Cancer Res., 51:4336–4341 (1991).
Berns, E.M.J.J., et al., Prostate, 9:247–259 (1986).
Langeler, E. G., et al., Prostate, 23:213–223 (1993).
Reddel, R. R., et al., Cancer Res., 48:1904–1909 (1988).
Webber, M. M., Normal and benign human prostatic epithelium in culture. In Vitro, 15:967–982 (1979).
Webber, M. M., In Vitro Models for Cancer Research (vol.V), pp. 25–125, Boca Raton, FL: CRC Press (1988).
Webber, M. M., Cell Biol. Internat. Rep., 4:185–194 (1980).
Rhim, J. S., et al., Proc. Natl. Acad. Sci. USA, 78:313–317 (1981).
Rhim, J. S., et al., Oncogene 4:1403–1409 (1989).
Rhim, J. S., et al., Science 227:1250–1252 (1985).
Cai, D., et al., Exp. Cell Res., 192:366–372 (1991).
Kleinman, H. K., et al., Biochemistry 25:312–318 (1986).
Albini, A., et al., Cancer Res., 47:3239–3245 (1987).
Grotendorst, G. R., Methods Enzymol., 147:144–152 (1987).
Chaproniere–Rickenberg, D.M., et al., A chemically defined medium for the growth of adult human pro–static epithelium. Cold Spring Harbor Symp. on "Growth of Cells in Hormonally Defined Media.",9B:1109–1115 (1982).
Schuurmans, A. L., et al., Int. J. Cancer, 42:917–922 (1988).
Webber, M. M., et al., In Vitro for Cancer Research, vol. V., pp. 3–24, Boca Raton, FL:CRC Press. (1988).
Bostwick, D. G., J. Cell. Biochem., 164:10–19 (1992).
Agarwal, C., et al., Cancer Res., 50:5947–5953 (1990).
Ruley, H. E., Nature, 304:602–606 (1983).
Quinlan, M. P., et al., Proc. Natl. Acad. Sci. USA, 84: 3283–3287 (1987).
Whyte, P., et al., Cell, 56:67–75 (1989).
Patterson, Methods Enzymol. 58:141 (1979).
MacDonald et al., Exp. Cell. Res. 50:471 (1968).
Thompson, Methods Enzymol., 43:308 (1979).
Hsu et al., Proc. Natl. Acad. Sci. USA 75:2003 (1978).

(List continued on next page.)

*Primary Examiner*—Mindy Fleisher
*Assistant Examiner*—James Ketter
*Attorney, Agent, or Firm*—Ian C. McLeod

[57] ABSTRACT

Immortalized non-tumorigenic or tumorigenic human prostatic epithelial and fibroblast cell lines and derivatives thereof, containing DNA of a hybrid virus between adenovirus 12 and simian virus 40. The cell lines are useful for research on causes, treatment and prevention of prostate cancer, benign prostatic hyperplasia, male infertility, birth defects, aging and assessment of environmental toxic agents.

21 Claims, 5 Drawing Sheets

OTHER PUBLICATIONS

Latt et al., In: Tice, R. R. and Hollaender, A., Sister Chromatic Exchanges, New York: Plenum Press, pp. 11 ff., (1984).

Stanbridge et al, Science 215:252–259 (1982).

Boring et al., CA, Cancer J. Clin. 44:7, 1994.

Lee et al., Internat. J. Oncol. 4, 821 (1994).

Rabson et al., Proc. Soc. Exper. Biol. Med. 116:187–190 (1964).

Fong, C.J., et al., Prostate, 21:121–131 (1992).

Antibodies: A Laboratory Manual., New York: Cold Spring Harbor Laboratory, pp. 359–413.

HUMAN PROSTATIC CELL LINES IMMORTALIZED BY ADENOVIRUS 12-SIMIAN VIRUS 40 (AD12/SV40) HYBRID VIRUS

GOVERNMENT RIGHTS

This application was funded under NIH Grant NIH 2 S07RR05656 23. The U.S. Government has certain rights under this application and any patent issuing thereon.

BACKGROUND OF THE INVENTION

1. Field of the Invention

The present invention relates to a novel immortalized epithelial cell line containing a hybrid virus and method for its preparation. In particular the present invention relates to a hybrid virus derived from adenovirus 12 and simian virus 40 viruses which is then used for the immortalization of the epithelial cells.

2. Description of Related Art

Human cells are generally difficult to grow and maintain in long-term cultures in vitro. They have a limited life span in culture, grow for a short time and usually after 4 or 5 subcultures, they senescence and die.

Prostate cancer is the leading cancer in men in the United States, in terms of incidence. Thirty-two percent (32%) of all cancers in men arise in the prostate. It is estimated that 200,000 new cases of prostate cancer will occur in the U.S. in 1994. Prostate cancer is the second leading cause of death from cancer and 38,000 deaths are estimated to occur in 1994 (Boring et al., CA, Cancer J. Clin. 44:7, 1994). African American men have the highest incidence of prostate cancer in the world, which is almost twice as high as that in white men and more than 600 times higher than in men from Thailand (Webber et al., In Vitro Models for Cancer Res. Vol. V, pp. 3–24, Boca Raton, CRC Press, 1988). One in 10 men in the U.S. will develop prostate cancer in their lifetime (by age 85). An estimated 11 million men have latent or clinical prostatic carcinoma. Sixty-five percent (65%) of the cases already have metastatic disease at the time of diagnosis. The survival rate is less than 20%.

The causes of prostate cancer are not known at the present time. A study of the causes, prevention and treatment has been hampered by the fact that good animal or cell models are not available. Although rat prostatic cells have been used extensively for such studies, rat prostate is not homologous to the human prostate, thus, it is not an ideal system to use.

There is a need for cell lines derived from normal human prostate which can be used for studies on the process of prostate cancer development in man and to identify agents which may cause or prevent prostate cancer.

Attempts have been made to immortalize human adult prostatic epithelial cells using a monkey virus (Simian virus SV40; Cussenot, O., et al., Journal of Urology 143, 881–886 (1991); Kaighn, M. E., et al, Cancer Research, 49, 3050–3056 (1989); Lee et al., Internat. J. Oncol. 4, 821 (1994)).

Infection of mammalian cells with Simian virus 40 (SV40) can have two outcomes. In some simian cells which allow multiplication of the virus and are hence called "permissive cells", infection results in virus production and ultimately in cell death. Cells which do not permit virus multiplication are designated as "non-permissive" cells, such as rodent cells. Infection of these cells leads to induction and maintenance of an altered "immortalized" phenotype at a low frequency. Invariably, an integrated copy of viral DNA (vDNA) persists.

The viral DNA in non-permissive, SV40-immortalized cells usually cannot be induced to excise itself and replicate, but virus can be induced to replicate after fusion of non-permissive cells with permissive simian cells. According to Gish et al (Gish, W. R., et al., J. Virol., 61:2864–2876 (1987)), two essential viral components for this excision and lytic replication are cis-acting origin of replication (ori) and a replication component A gene product (large T antigen) acting in trans.

In culture, many types of human cells are semi-permissive for SV40 replication. The semi-permissive response of human cells to SV40 infection appears to be complex. Human cells can be productively infected by the virus, but they yield 100 times less virus than the simian cells. A few cells, which survive the lytic infection, may pass through a crisis period to yield immortalized cell lines which carry integrated copies of vDNA (Gish, W. R., et al., J. Virol., 61:2864–2876 (1987)). During this period, the rate of cell multiplication is markedly reduced or ceases. It has also been observed that cultures of SV40-infected human cells that were nursed through crisis no longer produced infectious SV40, although they had done so prior to crisis (Girardi, A. J., et al., J. Cell. Comp. Physiol. 65:69–84 (1965)). Furthermore, survivors of crisis exhibited higher levels of T-antigen staining than they did prior to crisis. High levels of T-antigen may be necessary for survival of cells through crisis (Girardi, A. J., et al., J. Cell. Comp. Physiol. 65:69–84 (1965)).

Three human cell lines immortalized only by SV40 virus alone have been developed in recent years. Immortalization of human neonatal prostate epithelial cells by strontium phosphate transection method using a plasmid (pRSV-T) containing SV40 was first accomplished by Kaighn et al., (Kaighn, M. E., et al., Cancer Res., 49:3050–3056 (1989)). The plasmid pRSV-T was developed at the National Cancer Institute. It is an SV40 ori construct containing the SV40 early region genes and the Rouse sarcoma virus long terminal repeat (Gorman, C., et al., Science, 221:551–553 (1983)). These cells formed rapidly growing, multi-layered colonies within two weeks and according to the authors, there was little or no indication of crisis. These cells contain cytokeratins and SV40-T antigen. They do not produce tumors in nude mice.

Cussenot et al (Cussenot, O., et al., J. Urol., 143:881–886 (1991)) used a plasmid containing SV40 genome with defective replication origin (ori-) encapsulated into liposomes. The cells were shown to contain the SV40 genome. They express large T-antigen and are positive for cytokeratins (CK) 18 and 19, weekly positive for prostatic acid phosphatase (PAP) and prostate specific antigen (PSA) and negative for CK 14. These cells contain high affinity receptors for 5α-dihydrotestosterone (5α-DHT).

In work similar to that of Cussenot et al., (J. Urol. 143:881–886, 1991), Lee et al., (Internat. J. Oncol. 4:821, 1994) used a plasmid (pRNS-1) containing an origin-defective SV40 genome and a plasmid carrying the neomycin resistance gene. A cell line was established, however, this cell line has not been characterized with regard to its prostatic epithelial origin on the basis of androgen responsiveness. These investigators were unsuccessful in establishing an immortalized prostatic epithelial cell line using Ad12-SV40 hybrid virus.

Adenoviruses have the ability to extend the lifespan of mammalian cells. When rat embryo cells are infected with adenovirus-2 (AD-2) virus, a fraction of the cells show extended lifespan but infectious virus could not be isolated from them although viral DNA persisted, as recognized by hybridization with labelled probes (Gallimore, P. H., et al., J. Mol. Biol. 89:49–72 (1974)).

In 1964, Rabson et al., (Proc. Soc. Exper. Biol. Med. 116:187–190, 1964), reported that the growth of adenoviruses in African green monkey kidney (AGMK) cell cultures is enhanced following pre-infection with SV40 virus. Schell et al (Schell, K., et al., Proc. Natl. Acad. Sci. USA, 55:81–88 (1966)) observed that the oncogenicity was markedly enhanced when adenovirus-12 (AD-12) and SV40 were passed serially together for five or more passages in AGMK cells. During the course of their investigation, Schell et al., (Schell, K., et al., Proc. Natl. Acad. Sci. USA, 55:81–88 (1966)) found that hybridization of the two viruses occurred. This hybrid virus was used in the present invention. This is the first successful immortalization of human prostatic epithelial cells with Ad12-SV40 hybrid virus.

OBJECTS

It is therefore an object of the present invention to provide an immortalized normal human prostatic epithelial cell line. Further, it is an object of the present invention to provide an epithelial cell line which is useful for research in vitro. A further objective of the present invention is a method for conversion of a non-tumorigenic, immortalized cell into a tumorigenic cell by the introduction of an oncogene. Further, the present invention relates to methods and kits for screening carcinogenic agents or potential chemotherapeutic, chemopreventive, anti-invasive and anti-metastatic agents using an immortalized adult human prostate epithelial cell line. These and other objects will become increasingly apparent by reference to the following description and the drawings.

DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 3 is a microscopic photograph of PWR-1E cells in passage 30, stained with hematoxylin and eosin. These cells have an epithelial morphology (625X).

FIGS. 6A to 6D consist of microscopic photographs showing immunolabelling of cellular proteins in PWR-1E cells. Proteins were detected by immuno-avidin-biotin-peroxidase staining.

FIG. 6A is a microscopic photograph showing strong positive staining for cytokeratin 8.

FIG. 6B is a microscopic photograph showing strong positive staining for cytokeratin 18. This staining demonstrates that PWR-1E cells are of epithelial origin showing expression of cytokeratins characteristic of luminal prostatic epithelial cells.

FIG. 6C is a microscopic photograph showing absence of staining with antibody to desmin. Desmin is a cytoskeletal protein expressed in muscle cells. This absence of staining further demonstrates that PWR-1E cells are epithelial and not muscle cells.

FIG. 6D is a microscopic photograph showing absence of staining with antibody to Factor VIII. Factor VIII is expressed by endothelial cells. This absence of staining further demonstrates that PWR-1E cells are epithelial and not endothelial cells (625X).

Figure 1A:
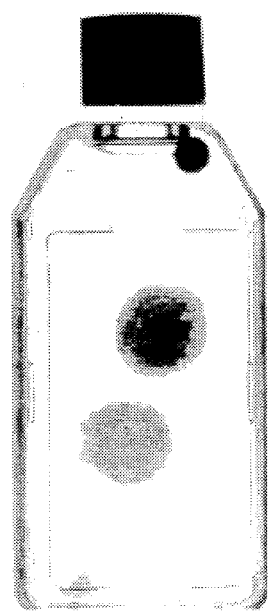
FIG. 1A is a photograph of a secondary culture of prostatic epithelium three months after infection with Ad12-SV40 virus. It shows two clones. PWR-1E cell line is a subclone of one of these.
Figure 1B:
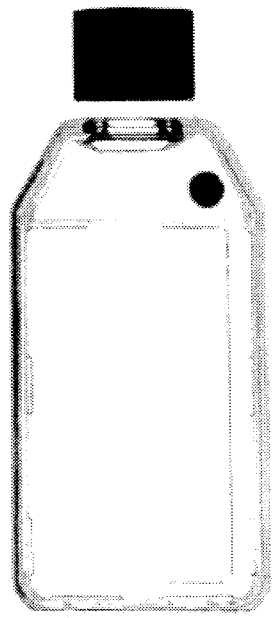
FIG. 1B is an uninfected control culture in which all cells have senescenced.

Southern blot analysis shows that PWR-1E carry the SV40 large T-antigen gene.

PWR-1E cells are not able to form colonies in soft agar. This demonstrates that, like normal cells, PWR-1E are anchorage dependent.

Ten (10) million PWR-1E cells were injected subcutaneously into nude mice. After 4 months none of the animals (0/3) developed tumors. This demonstrates that PWR-1E cells are not tumorigenic.

DESCRIPTION OF PREFERRED EMBODIMENTS

The present invention relates to an immortalized human prostatic epithelial or fibroblast cell line in culture, free of other cell lines, containing DNA of adenovirus and simian virus as a hybrid virus. This further includes immortalization and transformation with adenovirus E1A and E1B and simian virus 40 middle-T and large-T antigen genes. The cells can be made tumorigenic by introducing an activated, viral Ki-ras oncogene in the cells.

In particular, the present invention relates to a method for producing immortalized human prostatic epithelial or fibroblast cell lines which comprises: providing human prostatic epithelial or fibroblast cells; and infecting the cells with a hybrid virus derived from an adenovirus and a simian virus to thereby immortalize the cells.

Further, the present invention relates to a kit for screening carcinogenic, chemotherapeutic or chemopreventive agents comprising an immortalized human prostate epithelial cell line or derivative thereof containing DNA of adenovirus and simian virus as a hybrid virus.

Finally, the present invention relates to a method for testing carcinogenicity of an agent comprising culturing the hybrid virus-containing cell line with an agent suspected of being carcinogenic and determining formation of an abnormal cellular mass by said cell line, the formation of the abnormal cellular mass being indicative of carcinogenicity of said agent.

The epithelial cells containing the hybrid virus (PWR-1E) are deposited under the Budapest Treaty with the American Type Culture Collection in Rockville, Md. as ATCC CRL 11611. The adenovirus 12 is a publicly available deposit ATCC VR-863, is also described in Schell et al., Proc. Nat. Acad. Sci. 55:81–88, 1966, and is available from many research sources. The simian virus 40 is a publicly available deposit ATCC VR-239, is also described in Schell et al., Proc Nat. Acad. Sci. 55:81–88, 1966 and is available from many research sources.

The PWR-1E cells are of prostatic epithelial origin and express cytokeratins 8 and 18, which demonstrates their origin from the differentiated secretory cells. They do not express desmin, which further demonstrates their epithelial origin and excludes origin from muscle cells. They do not express Factor VIII, which excludes origin from endothelial cells. They were negative for virus production in a "cytopathic effect assay" in Vero cells (Rhim et al., Science 227:1250–1252, 1985). They show a moderate growth response to 5α-DHT and early passages, without androgen stimulation, were weakly positive for prostate specific antigen (PSA). Preliminary results show that these cells have a normal profile for the expression of plasminogen activators (urokinase and tissue-type plasminogen activator) and type IV collagenases.

EXAMPLE 1

1. Isolation and Culture of Prostatic Cells

Methods for isolation and maintenance of pure cultures of human prostatic epithelium were developed by Webber, (Webber, M. M., In vitro models for prostatic cancer: Summary. In: Models for prostate cancer, G. P. Murphy (ed.) pp. 133–147, New York, N.Y.: Alan R. Liss. (1980); Webber, M. M., Normal and benign human prostatic epithelium in culture. In Vitro, 15: 967–982 (1979); Webber, M. M., In Vitro Models for Cancer Research, Vol. V, pp. 25–125, Boca Raton, Fla.: CRC Press (1988); Chaproniere-Rickenberg, D. M. et al., Growth of Cells in Hormonally Defined Media, 9B:1109–1115, (1982)).

a. Isolation

Isolation and growth of human prostatic epithelium was accomplished according to methods described previously. The medium is serum-free and chemically defined. These studies have been described in detail elsewhere (Webber, M. M., In vitro models for prostatic cancer: Summary. In: Models for prostate cancer, G. P. Murphy (ed.) pp. 133–147, New York, N.Y.: Alan R. Liss. (1980); Webber, M. M., Normal and benign human prostatic epithelium in culture. In Vitro, 15:967–982 (1979); Webber, M. M., In Vitro Models for Cancer Research (Vol. V), pp. 25–125, Boca Raton, Fla.: CRC Press (1988); and Chaproniere-Rickenberg, D. M., et al., A chemically defined medium for the growth of adult human prostatic epithelium. Cold Spring Harbor Symp. on "Growth of Cells in Hormonally Defined Media.", 9B:1109–1115, (1982)).

The normal primary cultures and earlier passages of PWR-1E cells were grown in the serum-free KGM medium from Clonetics, San Diego, Calif., supplemented with antibiotic/antimycotic mixture from GIBCO 600-5240 PG, Grand Island, N.Y. (Penicillin 100U, Streptomycin 100 µg and Fungizone 25 µg,). Recent passages have been maintained in K-SFM, a serum-free, defined medium and antibiotic/antimycotic mixture from GIBCO K-SFM, No. 10005-018, Grand Island, N.Y. Cells have been frozen successfully and recovered with good viability. A tissue specimen of normal prostate from a 67 year old white male patient undergoing surgery for bladder cancer was used for epithelial cell isolation. Pathology report stated "normal prostate, mild nodular hyperplasia, no neoplasms". The tissue was cut into 2–3 mm cubes and placed in one 100 mm Petri dish with 30 ml RPMI-1640 containing 5% FBS (Intergen, No. 1050-75, Purchase, N.Y.), and 400 Units/ml of collagenase (GIBCO Cat. No. 840-701811, Grand Island, N.Y.) activity 196U/mg, antibiotics/ml as follows: Penicillin 100U, Streptomycin 100 µg and Fungizone 25 µg, Gentamycin 10µg). After 48 hr. digestion in collagenase, the tissue was triturated until all lumps were broken up, and centrifuged to remove collagenase. The pellet was suspended in Saline G and allowed to settle in the refrigerator for 1 hour. The sediment was suspended again and allowed to settle at 4° C. Four such washes were done. The sediment, after the last wash, containing the acini was suspended in storage medium containing spermine (2 µg/ml) and left at 4° C. overnight to destroy any fibroblasts that may be present in the preparation (Webber, M. M., Cell Biol. Internat. Rep., 4:185–194 (1980)).

b. Culture

The following day, the acini were centrifuged, suspended in growth medium and plated. Primary cultures of prostatic epithelium were established. Growth medium consisted of KGM (keratinocyte growth medium) from Clonetics No. CC-3001, San Diego, Calif. KGM has 0.2 mM calcium, 0.1 ng/ml EGF and pituitary extract. This medium was supplemented with 10 ng EGF/ml to make sure that the cells were not lost. Previous work has shown that prostate epithelial cells grow well with this EGF supplementation. To further ensure the survival of these cells, culture flasks/plates for growing these cells were coated with a mixture of 10 µg/ml each of fibronectin and collagen IV (Collaborative Research, No. 40008 and No. 40233, respectively). During the past year, we have been using K-SFM medium from GIBCO, Grand Island, N.Y. for maintaining the cell lines. This medium contains 0.09 mM calcium, 50 µg/ml pituitary extract and 5 ng/ml EGF with no other supplementation.

Primary cultures were subcultured using GIBCO Trypsin: EDTA mixture (0.05% trypsin, 0.02 mM EDTA, No. 25300-013) diluted 1:1 with PBS after one wash with ca/Mg-free Dulbecco's PBS. Cells were plated in coated plates. Medium was changed every third day. These cells were further subcultured to determine the number of passages until senescence and cell loss. These cells could not be propagated beyond five passages.

2. Immortalization by Infection with AD12-SV40 Hybrid Virus

Primary and secondary cultures were used for this infection. AD12-SV40 preparation (1:10 dilution) was used (Rhim, J. S., et al., Proc. Natl. Acad. Sci. USA, 78:313–317 (1981)). Several cultures were infected. Untreated control cultures were also maintained and medium was changed twice weekly. After 10 days the infected cultures were subcultured and plated in coated plates. Cells were fed every third day. One month after infection, colonies began to appear and some areas of the culture showed cytopathic effects, whereas, the control cultures showed signs of degeneration. Two weeks later, clones from infected cultures were isolated. These were plated into coated 24-well plates. Twenty-four (24) clones were isolated. One clone grew rapidly and was further propagated through several passages. This clone did not show any cytopathic effects and cells had an epithelial morphology. Cells from passage 10 were recloned by plating 1000 cells per 100 mm plate. Cloning efficiency of this population was 4.4%. These clones were further subcloned by dilution plating of single cells in 96-well plates. Sixty-six (66) clones were isolated and further propagated.

Figure 2:
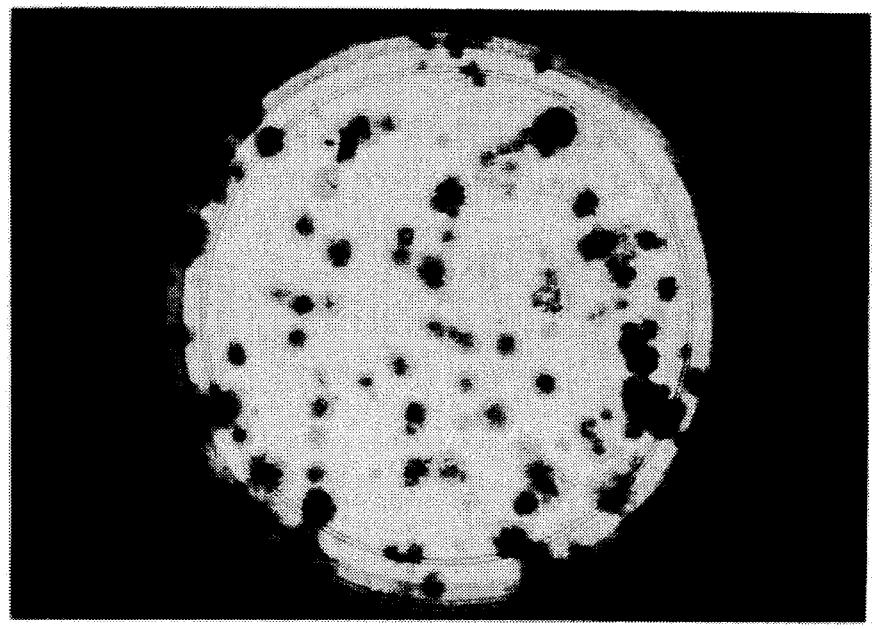
FIG. 2 is a photograph showing subcloning of a clone of epithelial cells described in FIG. 1A. This was done to ensure selection of a true clone. A sample plate (shown here) was fixed and stained with crystal violet 15 days after plating and cloning efficiency was also determined.
Figure 3:
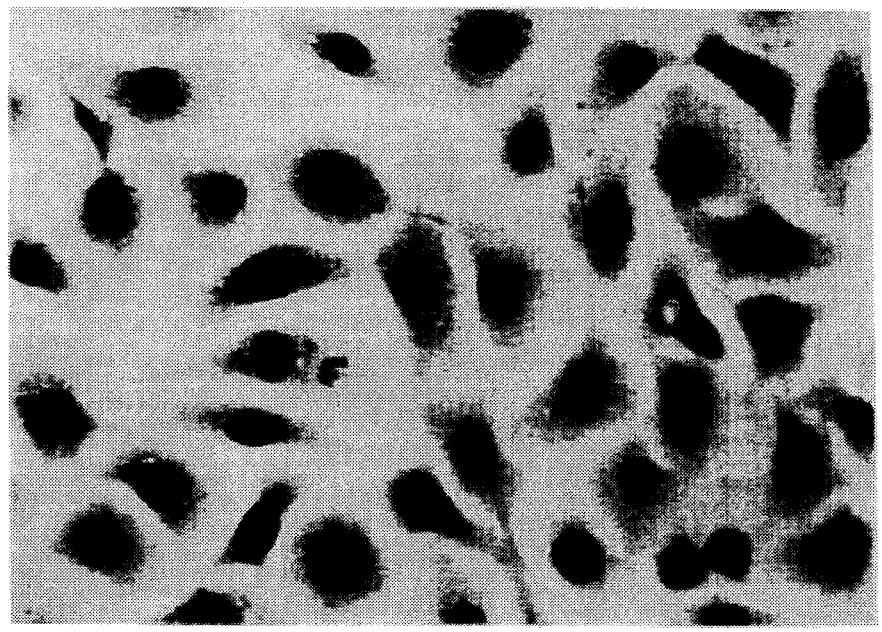
FIGS. 3, 6A, 6B, 6C and 6D are color photographs.

FIG. 2 shows the second cloning of cells. From this cloning, an AD12-SV40 Immortalized, non-malignant cell line, designated as PWR-1E cells has been established. At present, passage 35 cultures of PWR-1E cells show epithelial morphology, and they are of a uniform size and shape. The cell sheets look excellent in terms of morphology. The cultures do not show any cytopathic effects. These cells have undergone over 250 cell generations.

The AD12-SV40 virus consists of recombinant DNA containing all or part of the SV40 genome and part or all of the adenovirus genome enclosed in adenovirus capsids. The AD12-SV40 hybrid virus was found to be highly oncogenic in newborn hamsters.

An advantage of using AD12-V40 hybrid virus for immortalization is that cultures infected with the hybrid virus escape the extended "crisis" period, lasting as long as several months, experienced by cultures infected only with SV40 virus. This was demonstrated by Reddel et al., (Reddel, R. R., et al., Cancer Res. 48:1904–1909 (1988) using human bronchial epithelial cells. However, these cells did not express the adenovirus early region proteins E1A and E1B. Cells immortalized with adenoviruses retain many of the characteristics of parent normal cells (Emami, S., et al., Proc. Natl. Acad. Sci. USA, 86:3194–3198 (1989)).

Immortalization with Ad12-SV40 hybrid virus is especially important when one analyzes the process of immortalization and malignant transformation by oncogenic DNA viruses. Adenovirus and SV40 viruses encode certain proteins which are associated with the ability to immortalize and induce malignant transformation.

Once the cells were immortalized, an extensive characterization of immortalized cells was essential before they could be used as a cell model system as follows.

EXAMPLE 2

1. Characterization of Cells on the Basis of Intermediate Filament and Other Proteins PWR-1E cells were characterized first to establish their epithelial origin on the basis of keratin expression. Expression of cytokeratins 8/18 pair associated with prostatic epithelial cells was examined. PWR-1E cells showed strong expression of both cytokeratins 8 and 18. The presence of keratins 8 and 18 proves, beyond doubt, the epithelial origin of PWR-1E cells and eliminates the possibility of fibroblastic origin since fibroblasts do not express keratins.

Intermediate filaments (IFs) are an essential component of the developmental program of different cell lineages (Sommers, C. L., et al., Cancer Res., 52:5190–5197 (1992)). By knowing the IF proteins expressed by cell lines, it becomes possible to characterize the origin of the cells. For example, cells of simple epithelia coordinately express certain cytokeratins. Thus, IFs can serve as useful markers for characterization of cells. IFs are constituents of virtually all differentiated cells and are one of the components of the cell cytoskeleton expressed in a tissue specific manner (Sommers, C. L., et al., Cancer Res., 52:5190–5197 (1992)). Cells of epithelial origin normally express cytokeratins while those of mesenchymal origin express vimentin IFs (Sommers, C. L., et al., Cancer Res., 52:5190–5197 (1992)). In addition to cytokeratin expression in PWR-1E cells, expression of other IF proteins was also examined to make certain that our cell line did not originate from any cell type other than prostate epithelium.

a. Cytokeratins

An important index of differentiation is the pattern of cytokeratin expression. Keratins are expressed in a cell and tissue-specific manner and their expression is known to change in abnormal differentiation processes. A human keratinocyte cell line KER-1 immortalized with large-T antigen gene shows a cytokeratin profile similar to that of non-immortalized keratinocytes except that KER-1 cells express higher levels of cytokeratins 13 and 19 (Agarwal, C, et al., Cancer Res., 50:5947–5953 (1990)).

Normal epithelial cell differentiation is marked by the production of distinct cytokeratin IFs. They consist of a family of about 20 polypeptides in the Mr range of 40 kDa to 70 kDa that are translated from distinct mRNAs derived from a large multigene family. All epithelial cells co-express at least one pair of cytokeratins, consisting of an acidic and a basic protein and these associate to form the IFs (Molloy, C. J., et al., Exp. Mol. Pathol., 49:128–140 (1988)). As epithelial cells differentiate, additional keratins are expressed or some may cease to be expressed. Thus, the appearance of specific cytokeratins is also a useful marker for identifying the level of differentiation (O'Guin, W. M., Schermer, A., Lynch, M. and Sun, T.: Differentiation-specific expression of keratin pairs. In: Cellular and Molecular Biology of Intermediate Filaments, R. D. Goldman and P. M. Steinert eds.), New York, Plenum Press, pp. 301–334, 1990. Cytokeratin expression can serve as a unique marker for prostatic epithelial cell differentiation (Sherwood, E. R., et al., Prostate, 18: 303–314 (1991)). The prostatic epithelium is a simple epithelium, consisting of less differentiated basal cells and more differentiated luminal cells with a specialized secretory function (Sherwood, E. R., et al., Prostate, 18:303–314 (1991)). CK 8 and 18 have been identified as luminal cell specific markers and CK 5 and 15 as basal cell specific marker pair. CK 8, a 52 kDa basic protein, pairs with the acidic CK 18 (Mr 45 kDa). Overwhelming data show that the selective co-expression of CKs is highly conserved in various epithelial lineages.

b. Desmin

To prove that the PWR-1E cells are not of smooth muscle origin, expression of desmin was examined. Epithelial cells should not express desmin. Desmin (Mr 53 kDa) IFs are found in smooth muscle cells (SMC), and in skeletal and cardiac muscle. A broad range of soft tissue tumors, e.g., sarcomas express desmin but carcinomas and melanomas do not. Desmin has not been found in normal epithelia or epithelial tumors (Truong, L. D., et al., Am. J. Clin. Pathol., 93: 305–314 (1990)). PWR-1E cells were negative for desmin. This demonstrates that PWR-1E cells are epithelial in origin.

2. Characterization on the Basis of Differentiated Functions of Prostatic Epithelial Cells a. Hormonal Response In vivo the growth and functional response of prostatic epithelium to androgens is reflected by limited stimulation in cell proliferation and the expression of PSA, PAP (Lin, M.-F., et al., Cancer Res., 52:4600–4607 (1992); and Fong, C.-J., et al., Prostate, 21:121–131 (1992)). Secretion of both PSA and PAP responds to androgen stimulation. The presence of androgen receptor would be another marker for establishing prostatic epithelial origin. Therefore, effect of 5α-DHT on the growth of PWR-1E cells, the expression of PSA and PAP and the presence of androgen receptor are being examined. It should however be emphasized that many transformed cell lines derived from hormone responsive normal cells lose hormone receptor and their ability to respond to that specific hormone. Examples include DU-145 and PC-3 human prostate carcinoma cell lines (Webber, M. M., In vitro models for prostatic cancer: Summary. In: Models for prostate cancer, G. P. Murphy (ed.) pp. 133–147, New York, N.Y.: Alan R. Liss. (1980)).

Very few studies have been done on the effects of 5α-DHT on the growth of normal human prostatic epithelium. Prostatic epithelial cells will grow in culture in the absence of androgen, however, they are androgen responsive. In one of her earlier studies, Webber has shown (Webber, M. M., In vitro models for prostatic cancer: Summary. In: Models for prostate cancer, G. P. Murphy (ed.) pp. 133–147, New York, N.Y.: Alan R. Liss. (1980)) that the growth of normal human prostatic epithelium was stimulated three to four fold in the presence of 0.3 µM 5α-DHT (Webber, M. M., Growth and maintenance of normal prostatic epithelium in vitro—A human cell model. In: G. P. Murphy, A. A. Sandberg and J. P. Karr (eds.), Models for Prostate Cancer, pp. 181–216, New York: Alan R. Liss. (1980)). The majority of studies on the effects of androgens on prostatic cells in culture have been done using the prostatic carcinoma cell line LNCaP. Generally in culture, 5α-DHT doses considerably higher than those that induce cell proliferation cause increased secretion of PSA and PAP proteins. For example, the earliest studies by Horoszewicz et al on LNCaP cells showed a 1.9 fold stimulation of cell growth with 1 nM to 0.1 µM 5α-DHT in cultures containing charcoal stripped serum. These cells also contained 210 fmol androgen receptor/mg cytosol protein (Horoszewicz, J. S., et al., Cancer Res., 43: 1809–1818 (1983)). They observed increase in PAP secretion at the entire range of 5α-DHT tested. However, much variation exists amongst results reported in different studies. Hasenson et al (Hasenson, M., et al., Prostate, 7:183–194 (1985)) observed only a weak cell proliferation response in LNCaP cells to 10 to 100 nM 5α-DHT and found only 16 fmol androgen receptor/mg protein. de Launoit et al., (de Launoit, Y., et al., Cancer Res., 51:5165–5170 (1991)) observed a biphasic effect on LNCaP cell proliferation with a maximum stimulation at 0.1 nM 5α-DHT and reduced cell proliferation to normal levels at higher concentrations. Simard et al. (Simard, J., et al., Cancer Res., 51:4336–4341 (1991)) observed stimulation of cell proliferation at 0.5–1 nM 5α-DHT after a 10 day exposure and an increase in apolipoprotein D secretion at 5 nM to 1 µM. Other investigators have studied the effects of the non-metabolizable, synthetic androgen R1881. Growth stimulation was observed from 0.1 nM to 0.1 µM (Berns, E. M. J. J., et al., Prostate, 9:247–259 (1986); and Langeler, E. G., et al., Prostate, 23:213–223 (1993)). At 1 nM and higher concentrations, stimulation of PAP secretion was observed (Langeler, E. G., et al., Prostate, 23:213–223 (1993)). These differences in hormonal response in different studies may be due to different culture conditions, different sublines or vastly different passages of LNCaP that may have been used in different studies. Other reasons may be the rapid metabolism of 5α-DHT in cell cultures. Berns et al observed that ~50% of the added (25 nM) 5α-DHT is metabolized within 2 hours in prostate cell cultures. They also showed that the proliferative response of cells also depended on the cell number plated (Berns, E. M. J. J., et al., Prostate, 9:247–259 (1986)).

b. Assay for Responsiveness to Androgens

Figure 5:
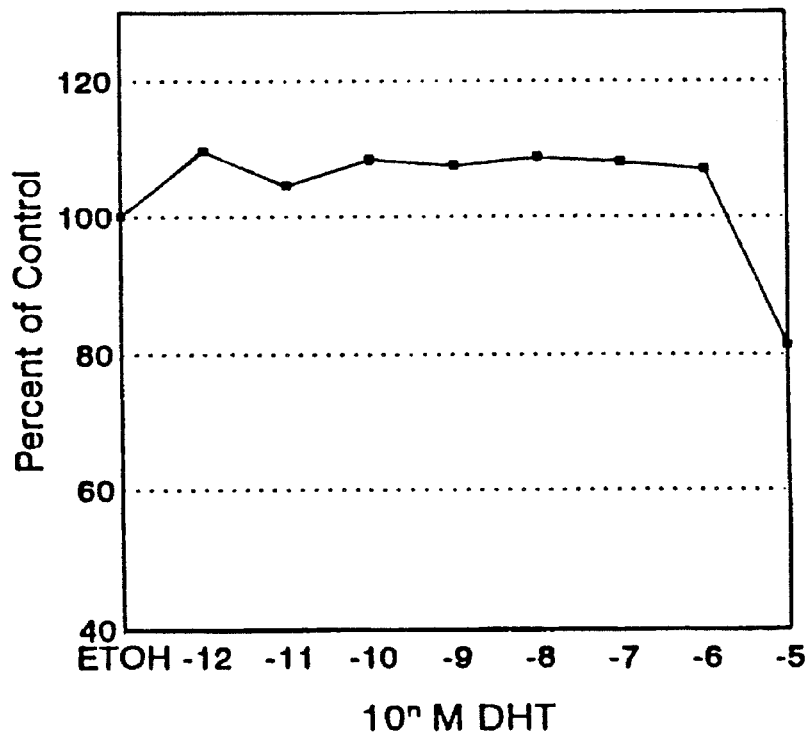
FIG. 5 is a graph showing the growth of PWR-1E in the presence of 5α-dihydrotestosterone (5α-DHT). Ten thousand (10,000) cells were plated per well of a 96-well microplate and exposed to varying concentration of 5α-DHT ($10^{-12}$M to $10^{-5}$M). 5α-DHT was dissolved in ethanol. PWR-1E cells show a growth response to 5α-DHT in culture.
Figure 6A:
Figure 6B:
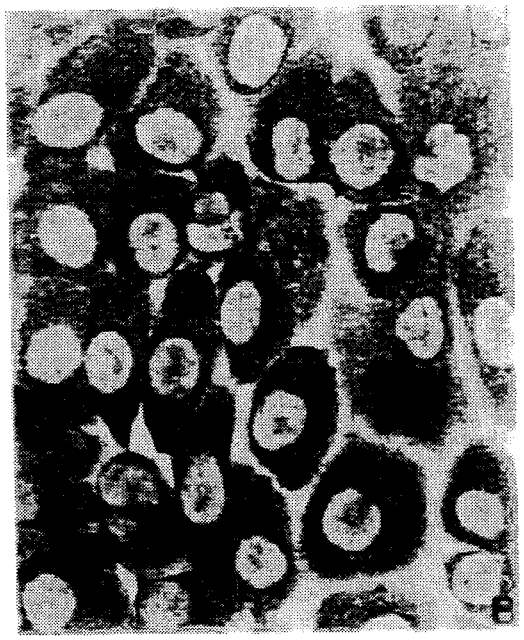
Figure 6C:
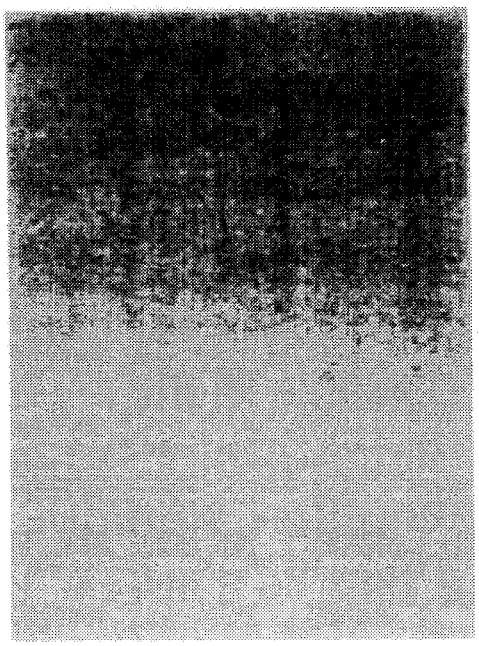
Figure 6D:
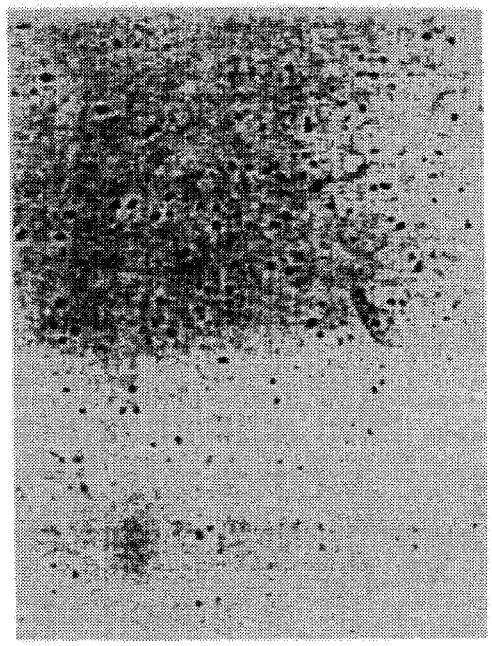

A microplate assay for establishing effects of androgens on the growth of cell lines was used. This assay has been routinely used by Webber and other study growth modulation (Cai, D., et al., Exp. Cell Res., 192:366–372 (1991)). 5,000 or 10,000 cells were plated/well of a 96-well plate in 200 µl of serum-free K-SFM. After 24 hours, medium was changed to media containing a range of concentrations of 5α-DHT. Medium containing 5α-DHT was changed every 48 hrs. Test plates were taken after 7 and 9 days of treatment and stained with the protein-binding dye, methylene blue. Bound dye was released with 1% sodium dodecyl sulfate (SDS) and absorbance measured at 620 nm with a microplate reader according to a method described earlier (Cai, D., et al., Exp. Cell Res., 192:366–372 (1991)). The results are shown in FIG. 5.

The prostatic epithelial origin of PWR-1E cells was confirmed by examining PSA and PAP expression, responsiveness to androgens and the presence of androgen receptor. It should, however, be noted that the immortalized neonatal prostatic cell line developed by Kaighn et al (Kaighn, M. E., et al., Cancer Res., 49:3050–3056 (1989)), does not express PSA or PAP and their prostatic carcinoma cell line also does not express PSA, expresses very low levels of PAP and is unresponsive to androgens (Kaighn, M. E., et al., Cancer Res., 49:3050–3056 (1989)). PWR-1E cells showed a moderate growth response to 5α-DHT treatment. Additional experiments are in progress using other, more stable androgens.

c. Differentiation

Differentiated, secretory prostatic epithelial cells secrete PSA and isozyme II PAP (Lin, M.-F., et al., Cancer Res., 52:4600–4607 (1992)). These proteins can be used as specific markers for establishing that the immortalized cells are: 1) of prostatic epithelial original, and 2) that they are capable of secreting these proteins, as they do in vivo. Both PSA and PAP are androgen responsive and their secretion can be modulated in androgen-responsive cells in vivo and in vitro, e.g., by exposure to 5α-DHT. The expression of these two proteins in response to "Mibolerone" a non-metabolizable androgen, and of androgen receptor in PWR-1E cells is being examined to demonstrate beyond doubt their prostatic epithelial origin. The primary and secondary cultures from which PWR-1E cells were derived, were positive for PSA.

It is important to note that a moderate growth response and PSA and PAP expression in response to 5α-DHT of cultures grown in serum-free medium may be due to the presence of epidermal growth factor (EGF) in the medium which is invariably a component of serum-free media. EGF is a potent inducer of cell proliferation in epithelial cells. It has been shown that addition of EGF to medium containing 5% fetal calf serum contributes to the loss of steroid binding (Schuurmans, A. L., et al., Int. J. Cancer, 42:917–922 (1988)). Experiments on 5α-DHT growth response and PSA and PAP expression were conducted in K-SFM medium (GIBCO, Grand Island, N.Y.) which contains 5 ng/ml EGF. These experiments need to be done using less or no EGF, if possible. This effect of EGF can be explained by the observation that cell proliferation and expression of differentiated function in response to androgens, such as 5α-DHT, have an inverse relationship.

PWR-1E cells express SV-40 large-T antigen. They were non-tumorigenic when tested for tumorigenicity in nude mice. They grow in a serum-free defined medium with a doubling time of about 40 hours.

d. Plasminogen Activator (PA) Expression

Differentiated prostatic epithelial cells normally secret both tissue-type (t-PA) and urokinase-type (u-PA) PAs which form an important component of the seminal fluid (Webber, M. M., et al., Retinoic acid modulates urokinase-type plasminogen activator expression in DU145 human prostate carcinoma cells. These enzymes can serve as an additional marker for prostatic epithelial function, especially as urokinase expression responds to testosterone exposure and could be used for early detection of prostate cancer. Expression of plasminogen activators and type IV collagenases in PWR-1E cells is similar to that in normal prostatic epithelium.

e. Assays for Plasminogen Activator Activity i. Zymography

Conditioned media from cultures of normal prostatic epithelium, PWR-1E cells and DU-145 human prostate carcinoma cells were subjected to SDS-PAGE zymography. Results show that the level of u-PA activity in PWR-1E cells is similar to that in normal cells, whereas, the malignant cells express considerably higher levels of u-PA.

ii. Chromogenic Substrate Assay

The activity of urokinase (u-PA) in conditioned media was also determined by a chromogenic substrate assay where the increase in absorbance of the free chromophore generated was measured and compared to the original u-PA specific substrate per unit time at 405 nm. At excess substrate concentration, the rate of absorbance increases due to the amount of chromophore released and is linearly related to enzyme concentration (Webber, M. M., et al., A. Retinoic acid modulates extracellular urokinase-type plasminogen activator activity in DU-145 human prostate carcinoma cells).

f. Type IV Collagenase Expression

Secretion of type IV collagenase was examined using SDS-PAGE zymography using gelatin or type IV collagen as substrates and samples of conditioned medium from PWR-1E cells cultures were tested. Preliminary results show that collagenase expression in PWR-1E cells is similar to that in normal prostate epithelial cells. These results provide one more normal characteristic maintained by PWR-1E cells.

EXAMPLE 3

1. Isozyme Analysis

Human origin of PWR-1E cells was established by isozyme analysis. PWR-1E cells have the following isozyme profile: LDH, human (lactate dehydrogenase); NP, human (purine nucleoside phosphorylase); G6PD, B (glucose-6-phosphate dehydrogenase); PGM1, 1 (phosphoglucomutase-1); PGM3, 1 (phosphoglucomutase-3); ESD, 1 (esterase D); Me-2, 0 (malic enzyme, mitochondrial); AK-1, 1 (adenylate kinase); GLO-1, 2 (glyoxalase-1).

2. Karyotype Analysis

A complete chromosome analysis was performed to establish that the cells are of human male origin. Chromosome number, presence of the Y chromosome, stable translocations, marker chromosomes and G-banding pattern were examined.

The cell line is aneuploid human male, with most chromosome counts in the hypotriploid range. A normal Y chromosome is present in about 20% of metaphases. Normal chromosomes #1, #2, #9, #14, #16, #17, #18, and #22 are most often trisomic; chromosomes #5, #15, #20, and #21 are usually tetrasomic; while the remainder of normal chromosomes are usually disomic. Cytogenetic alterations, other than copy number, are not prominent: most chromosomes are normal. Cells other than those of cell line PWR-1E p17 were not detected in the culture. They are hypotriploid and carry a Y chromosome. Twenty percent (20%) of the cells contain a normal Y chromosome.

3. Cytopathic Effects Assay in Vero Cells

The PWR-1E cells were tested for free virus production, using this assay in the sensitive Vero cells (Rhim, J. S., et al., Science, 227:1250–1252 (1985)). This assay was performed to establish that PWR-1E cells were a non-producer cell type. Only those immortalized cells that have an integrated viral genome and are not shedding the virus are useful. The Veto cell line is derived from the kidney of a normal, adult African green monkey. Vero cells (ATCC CCL 81) are permissive for the growth of SV40 and adenoviruses which results in a lytic infection of cells, producing cytopathic effects (CPE).

Vero cells were grown in Dulbecco's MEM with 5% fetal bovine serum. Ten thousand (10,000) Vero cells were plated per well in 6-well plates. At 50% confluency, cultures were inoculated, in duplicate, with 500 µl of undiluted and diluted (1:2, 1:4, 1:8, 1:10), four-day conditioned medium from PWR-1E cells. Cells were maintained for 21 days and observed periodically for cytopathic effects. Conditioned medium from PWR-1E cells did not cause CPE in Vero cells, hence, they are a non-producer cell line.

4. Growth Curves

Figure 4:
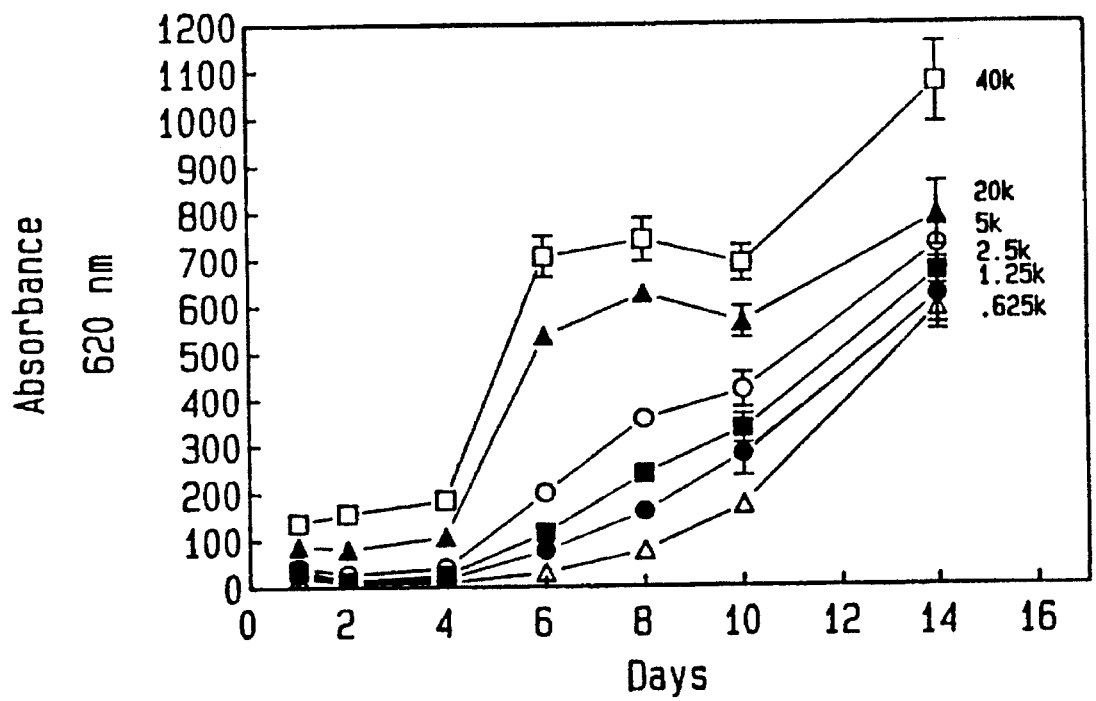
FIG. 4 is a graph showing growth of PWR-1E cells. Cells were plated at densities varying from 625 cells/well to 40,000 cells/well, in 96 well plates. Plates were fixed and stained with Methylene blue and absorbance measured at 620 nm earlier (Cai et al., Exper. Cell Res. 192:366, 1991).

Cells were plated in 96-well plates at different densities varying from 625 cells to 40,000 cells per well in triplicate. Medium was changed every 48 hours. Plates were taken at 48 hr. intervals, beginning with 2 days after plating, fixed, stained and prepared for reading absorbance as described earlier (Cai, D., et al., Exp. Cell Res., 192:366–372 (1991)). Growth curves for PWR-1E cells are shown in FIG. 4. These cells have a doubling time of about 40 hrs.

5. Immunoperoxidase and Immunofluorescence Methods

Expression of cytokeratins, desmin, Factor VIII, PSA and PAP protein expression was detected using monoclonal antibodies (MoAbs) and avidin-biotin immunoperoxidase (Vector ABC kit No. PK-6102) or immunofluorescence methods (Antibodies: A Laboratory Manual., New York: Cold Spring Harbor laboratory, pp. 359–413, (1988)). MoAbs are available for all of the antigens to be tested, from Sigma, St. Louis, Mo. (CK 8, No. C-5301; CK 18, No. C-8541,) and Dako, Carpinteria, Calif. (Desmin, No. D-1033; Factor VIII, No. F-3520, PSA, No. M-750). Two different sets of cultures were tested for each cell line. Appropriate controls employing non-immune serum were used. The results are shown in FIGS. 6A to 6D.

6. Agar Assay for Anchorage Independence

Normal cells do not form colonies in soft agar. Immortalized PWR-1E cells did not form colonies in agar. Thus, like normal cells, they are anchorage dependent, while the malignant cells will be expected to form colonies. DU-145, human prostate carcinoma cells, form colonies in agar, and are used as a positive control. Colonies of anchorage independent cells appear in 3–5 weeks.

7. Growth in Nude Mice

Ten (10) million cells were injected subcutaneously in 3 mice. Mice were examined periodically for tumor development and were maintained for four months. After four (4) months, none of the 3 mice injected with PWR-1E cells had developed tumors at the site of injection. Hence, PWR-1E cells are not tumorigenic.

8. Lack of Invasive Ability

It was anticipated that the immortalized cells would not be invasive in an in vitro invasion assay using our constituted basement membrane. Results show that PWR-1E cells are non-invasive as compared to carcinoma cell lines.

a. In Vitro Assay for Invasive Potential of Cells

This assay involves the use of Boyden chambers where cells plated on top of a porous filter coated with a reconstituted basement membrane "matrigel," in the upper chamber were allowed to invade and migrate through matrigel for a period of 6 hrs. The lower chamber contained fibroblast conditioned medium as a chemo-attractant. The speed of migration correlates with the invasive potential (Webber, M. M., et al., A. Retinoic acid modulates extracellular matrix degradation mediated by proteases secreted by prostatic carcinoma cells, Kleinman, H. K., et al., Biochemistry 25:312–318 (1986); Albini, A., et al., Cancer Res., 47:3239–3245 (1987)). Cells migrate to the underside of the filter, which are then stained on the filter with HEMA 3 (Curtin Matheson, Houston, Tex., USA). The nuclear stain is then extracted with 0.1N HCl and absorbance is measured using a Microplate reader (Grotendorst, G. R., Methods Enzymol., 147: 144–152 (1987)). The number of cells migrated shows a correlation with absorbance.

9. Expression of Viral Antigens

The expression of SV40 large-T antigen in PWR-1E cells was examined. SV40 immortalized cells have been shown to carry the immortalizing, large-T antigen gene (Gish, W. R., et al., J. Virol., 61:2864–2876 (1987); and Reddel, R. R., et al., Cancer Res., 48:1904–1909 (1988)). PWR-1E cells express the large-T antigen.

10. Prostate Pathology

An analysis of the pathology of the prostate shows that the incidence of latent carcinoma of the prostate is about the same worldwide (Webber, M. M., et al., In Vitro Models for Cancer Research, Vol. V., pp. 3–24, Boca Raton, Fla.:CRC Press. (1988)). However, the high incidence American male population shows a higher percentage of more aggressive, invasive-type latent carcinomas which develop into clinical carcinomas, compared to low incidence populations which show less aggressive, non-invasive-type, latent carcinomas. New evidence indicates that the precancerous lesions appear at a young age in men in their twenties and thirties (Bostwick, D. G., J. Cell. Biochem., 164:10–19 (1992)). This suggests that there is a long latent period of 20 to 30 years before cancer develops. Early changes during this period are an excellent target for cancer prevention. The best cure for cancer is prevention. The availability of immortalized cell lines makes it possible to test agents which could be used for cancer prevention, starting at a young age when cancers appear to first originate.

EXAMPLE 4

1. Immortalization and the Phenomenon of Senescence

Senescence appears to be characteristic of all normal human cells in vivo and in culture. SV40 transformed human cells typically have extended in vitro lifespan but eventually reach a stage referred to as "crisis", where the cultures become static and cell proliferation is greatly reduced or ceases. The parent cultures of PWR-1E cells did not experience this crisis phase because cells infected with the hybrid virus escape the crisis stage.

Clone formation and immortalization were achieved at a high efficiency because the primary cells used for virus infection were grown in a serum-free medium. Many epithelial cells, especially epidermal-like cells are usually induced to terminally differentiate in serum-supplemented medium because TGF-β is a major serum-derived inhibitor (Stoner, G. D., et al., Cancer Res., 51:353–371 (1991)). As a result of this differentiation, many virus-infected cells would terminally differentiate and would be lost. Establishment of well characterized, human, non-malignant cell lines allows detailed investigation of many aspects of the normal prostatic epithelial cell physiology and of prostate tumors. Such immortalized and well characterized human prostate cell lines are not presently available. PWR-1E provides a useful tool to study the biology and the pathology of adult prostatic epithelial cells, specifically to understand the steps leading to prostatic transformation.

Malignant transformation of mammalian cells requires at least two separate functions i) the establishment function is concerned with immortalization of cells and ii) transformation function is required for full expression of an oncogenic phenotype (Ruley, H. E., Nature, 304: 602–606 (1983)). For example, Polyoma virus middle-T and the T24 Harvey ras 1 gene are unable individually to transform primary baby rat kidney cells. However, adenovirus early region E1A gene provides functions required by these genes to transform cells. Also, early region E1B is unable to transform cells in the absence of E1A. E1A immortalizes and E1B transforms, therefore, both are needed for malignant transformation. The immortalization step enables cells to respond to growth factors and to the action of transforming proteins (Ruley, H. E., Nature, 304: 602–606 (1983)).

2. Some Examples which Demonstrate the Cooperate Nature of Immortalizing and Transforming genes Human keratinocytes were immortalized by infection with AD12-SV40 hybrid virus. These cells are not tumorigenic. Subsequent infection with Kirsten murine sarcoma virus, i.e., with Ki-ras oncogene resulted in the acquisition of neoplastic properties. These results support the multistep process of carcinogenesis (Rhim, J. S., et al., Science, 227:1250–1252 (1985)). Neither control nor Ki-MSV infected cells could be propagated serially beyond 2 or 3 subcultures. In contrast, AD12-SV40 infection led to the appearance of actively growing colonies by 3 to 4 weeks. By week 6, T-antigen was revealed in the nuclei. Cells contained SV40 transcripts but not AD12. No transcripts were detected from adenovirus E1A and E1B regions in these transformed human cells (Rhim, J. S., et al., Science, 227:1250–1252 (1985)). Infection of primary baby rat kidney cells with adenovirus 5 resulted in increase in cell proliferation. These cells produced a growth factor which stimulated the growth of primary cultures (Quinlan, M. P., et al., Proc Natl. Acad. Sci. USA, 84:3283–3287 (1987)). Results suggest that E1A exerts its transformation potential through interactions with products of the tumor suppressor genes (Whyte, P., et al., Cell, 56:67–75 (1989)).

Chimpanzee skin fibroblasts immortalized with AD12-SV40 virus contained AD12 and SV40 antigens and produced virus. However, at passage 9, one line became non-producer and did not show virus-specific antigens. Hybrid virus could not be rescued from these cells by co-cultivation with Vero cells ((Rhim, J. S., et al., Proc. Natl. Acad. Sci. USA 78:313–317 (1981)).

In summary, we have established an AD12-SV40 immortalized cell line PWR-1E, derived from human prostatic epithelium. PWR-1E cells express many characteristics of normal epithelial cells and are non-tumorigenic cells. Cells show a growth response to 5α-DHT. Experiments to accomplish further characterization are in progress. These cells provide an important model for studies on prostate carcinogenesis.

The following description demonstrates the significance of the novel non-malignant cell lines: The applications for the cell lines are in the areas of causes, prevention and treatment of prostate cancer and of benign prostatic hyperplasia (BPH); role of diet and nutrition in cancer; aging research; cell physiology; studies on the mechanisms of secretion; cell biology; biochemistry; studies on cell differentiation; developmental biology; and all biomedical sciences.

1. Acquisition of Normal Human Tissue

Specimens of normal human prostate are very difficult to obtain because of the availability and consent concerns. Since PWR-1E cells retain many characteristics of normal cells, they may be used in experiments in place of normal cells, which are generally not available to most investigators.

2. Human Cell Models

Use of human cell models is considered much more appropriate than using rat or mouse cells, data from which then have to be extrapolated to the human condition.

3. In Vitro Models

Use of cell models for research is preferred as much as possible in order to avoid unnecessary use of whole animals.

The cell lines can be used for research in the following and other areas:

4. Cancer Detection and Diagnosis

As models for the discovering new markers for early detection of prostate cancer and BPH.

5. Cancer Treatment (a). The cells, transformed as described above, can be used as cell systems for the discovery of new drugs such as cisplatin and taxol for the treatment of prostate cancer and BPH.

(b). As cell models for examining the efficacy of single drugs and combination of drugs and/or radiation for the treatment of prostate cancer.

(c). As cell systems for identification of anti-invasive agents, such as protease inhibitors, i.e., inhibitors of urokinase and type IV collagenase, and other agents which can specifically prevent invasion, including anti-motility factors, and thus can be used to prevent cancer from invading the neighboring tissue.

(d). As cell models for the identification of anti-metastasis agents, which can specifically prevent cancer from spreading to distant organs.

(e). As cell models for the identification of anti-angiogenic agents, which can specifically prevent growth of new blood vessels into the tumor.

6. Cancer Prevention

As models for the discovery and testing of agents which may have the ability to prevent prostate cancer and benign prostatic hyperplasia.

7. Basic Research

The cell models can be used for a large variety of studies, for example:

(a). The immortalized human prostatic cells are especially useful for studying the etiology and multistep process of carcinogenesis in the prostate. This immortalized prostatic cell line, capable of growth in serum-free medium, is useful for studying neoplastic transformation and the multistep process of carcinogenesis involving initiation and promotion in the prostate and for investigating the action of putative prostatic carcinogens. This may include oncogenes, chemical carcinogens and promoters, and radiation. These cells can also be used for the identification of carcinogenic agents and the process of cancer development in the human prostate.

(b). For the identification of agents which cause benign prostatic hyperplasia and the process of BPH development.

(c). For the identification of specific genetic defects, in the multi-step process of carcinogenesis, which lead to the development of prostate cancer.

(d). For studies on why prostate cancer does not respond well to chemotherapy.

(e). For studies on the mechanisms of drug resistance in prostate cancer and how to circumvent resistance.

(f). Cells immortalized with this hybrid virus can be used to study:

i. The interactions between the tumor suppressor gene encoded host cell proteins, such as p53 and pRB and the viral immortalizing genes such as adenovirus E1A and SV40 large-T antigen. As shown in Table 1, viral proteins are able to bind and sequester the suppressor proteins, thus, allowing uncontrolled growth. The E1A and SV40 large-T antigens prevent the suppressor proteins from performing their normal function, which is to suppress cell proliferation. Loss or abnormal expression of p53 or pRB is associated with increased risk for cancer.

ii. The role played by suppressor genes in prostate cancer.

iii. The multistep process of carcinogenesis in the human prostate.

iv. Escape from senescence, i.e., immortalization. This is important not only for improving our understanding of the aging process but also of cancer since malignant transformation results in the development of immortal cells.

TABLE 1

| Viral protein | Suppressor gene protein |
| --- | --- |
| SV40 large T antigen | p53, pRB |
| E1A of adenovirus | pRB |
| E1B of adenovirus | p53 |

Normal cells undergo senescence and are lost. However, immortalization with AD12-SV40 allows a study of escape from aging and death. SV40 infected human cells go through a "crisis" phase which may last a year or more, whereas, cells infected with the hybrid virus escape this crisis phase and clones of immortalized cells can be selected rapidly. Since prostate cancer incidence increases with age, this cell model would be especially useful for studies on aging and acquisition of immortality.

(g). Basic understanding of prostate physiology and its role in reproduction.

8. Mechanisms of Tumor Progression

Tumor progression itself is a multi-step process which includes invasion, metastasis, angiogenesis and the development of drug resistance. The expression of proteases such as urokinase and collagenase, is associated with progression. The cells can be used for studies, for example:

(a). The mechanism of tumor progression and the associated genetic and epigenetic changes.

(b). Increased expression of the above mentioned proteases and their appearance in the blood of cancer patients may serve as an indicator/marker of the advanced stage of the disease. Thus, the cell lines can be used for the identification of agents which decrease or modulate protease activity and thus, may be useful cancer prevention, intervention and therapeutic agents. These agents include anti-invasive and anti-metastatic agents. Levels of these proteases in the blood could also be used as indicators of treatment efficacy.

(c). Tumor progression is also associated with angiogenesis. These cell lines can be used for the identification of anti-angiogenic agents.

9. Models for Risk Assessment of Reproductive Toxicity

Reproductive toxicity may result in infertility in men, spontaneous abortions in their female partners and birth defects in their offspring. This cell line and derivatives thereof, can be used as:

(a). A model for identification of reproductive toxins which may be secreted into the seminal fluid and thus, damage sperm, resulting in abortions and birth defects.

(b). A model for detection of exposure to environmental and industrial reproductive toxins.

(c). A model for detection of reproductive toxicity in men exposed to chemicals in chemical warfare.

(d). A model for infertility and for birth defects in the offspring of men exposed to toxic chemicals in the industry and in chemical warfare.

(e). A model for studies on organ specific toxicity, and especially for studies on the transport of toxins into the seminal fluid by prostatic cells. This cell model would be useful for studying uni-directional transport and secretion of toxins into the seminal fluid and their effect on sperm. For instance, evidence is accumulating to suggest an association of pesticides with birth defects and cancer. Some of these toxins may be passed to infants via human milk. Others may damage sperm by their presence in the prostatic fluid which provides a vehicle for sperm. The availability of well characterized human prostatic epithelial cell lines will provide useful models for studies on infertility and birth defects.

10. Cells to be Used as "Normal" Controls, when Samples of Human Prostate are not Available These cells retain many characteristics of normal epithelial cells, e.g., normal cytokeratin expression of cytokeratins 8 and 18, absence of desmin or Factor VIII expression, contact inhibition and monolayer formation in culture, response to 5-α dihydrotestosterone, anchorage dependence and inability to grow in agar, inability to form tumors in nude mice and normal protease profiles. Since PWR-1E cells express many of the characteristics of normal differentiated prostatic epithelial cells, they can be used for certain studies in place of normal human prostatic epithelial cells, which are very difficult to acquire. This is a useful model for those studying the processes of cell secretion, for example, in cystic fibrosis patients.

11. Studies on Uni-directional Transport of Secretory Proteins

PWR-1E cells are useful for studying such differentiated functions as uni-directional transport and secretion of prostate specific proteins.

12. Identification of Potential Chemotherapeutic Drugs

These cells are useful for screening chemicals suitable for the treatment of cancer and related diseases, by growing them in vitro in medium containing the chemical to be tested and then, after a suitable period of exposure, determining whether and to what extent cytotoxicity has occurred, e.g. by trypan blue exclusion assay or related assays (Patterson, Methods Enzymol. 58:141 (1979)), or by growth assays such as colony forming efficiency (MacDonald et al., Exp. Cell. Res. 50:417 (1968)), all of which are standard techniques well known in the art.

Similarly, potential chemotherapeutic drugs may be screened in vivo in suitable animal models. The tumorigenic or nontumorigenic human prostate epithelial cell lines are injected subcutaneously into athymic nude mice. Potential chemotherapeutic drugs are injected at various time intervals and doses. Animals are examined weekly for the presence of tumors for a period of four or more months.

13. Studies of Metabolism of Carcinogens and other Xenobiotics

Carcinogens and other xenobiotics may be added to the growth medium of cultures of these cells and then the appearance of metabolic products of these compounds may be monitored by techniques such as thin layer chromatography or high performance liquid chromatography and the like. The interactions of the compounds and/or their metabolites with DNA can then be examined.

14. Studies of DNA Mutagenesis

Substances known or suspected to be mutagens may be added to the growth medium of cultures of PWR-1E cells and then mutations may be assayed, e.g., by detection of the appearance of drug resistant mutant cell colonies (Thompson, Methods Enzymol., 48:308 (1979)). Similarly, cell-mediated DNA mutagenesis in PWR-1E cells can be examined by co-cultivating them with a cell type known to have the ability to activate a procarcinogen and, thus, release mutagenic metabolites into the culture medium (Hsu et al., Proc. Natl. Acad. Sci. USA 75:2003 (1978)).

15. Studies of Chromosome Damaging Agents

Substances known or suspected to cause chromosomal damage may be added to the culture medium of these cell lines, and then the extent of chromosomal damage may be measured by techniques such as measurement of the frequency of sister chromatid exchange (Latt et al. In: Tice, R. R. and Hollaender, A., Sister Chromatid Exchanges, New York: Plenum Press, pp. 17–40, (1982)).

16. Studies of Malignant Transformation

By chemical, physical and viral agents, and transferred genes including oncogenes and high molecular weight genomic DNA from tumors, using standard assays such as tumor formation in athymic nude mice.

17. Studies of Cellular Responses to Growth Factors and Production of Growth Factors Identification and purification of novel growth factors important for growth and differentiation of human prostate epithelial cells. These cells are particularly useful for such an application since they grow in serum-free media. Therefore, responses to growth factors can be studied in precisely defined growth media and any factors produced by the cells may be identified and purified without the complication of the presence of serum.

18. Use of Recombinant DNA Expression Vectors to Produce Proteins of Interest For example, the gene encoding a protein of therapeutic value may be recombined with controlling DNA segments (i.e. containing a promoter with or without an enhancer sequence), transferred into the cell (e.g. by polybrene transection) and then the protein produced may be harvested from the culture supernatant or a cellular extract by routine procedures well known in the art.

19. Characterization of Cell Surface Antigens

The cells are incubated with an antibody against the cell surface antigen of interest, and then reacted with a second antibody which is conjugated to a fluorescent dye. The cells are then evaluated using a fluorescence activated cell sorter to determine whether they are fluorescent and therefore possess the cell surface antigen.

20. Cell-cell Hybrid Studies for Identification of Tumor Suppressor Activity (Stanbridge et al, Science 215:252–259 (1982))

To determine whether immortalized non-malignant cell lines contain tumor suppressor genes, they are fused to malignant tumor cells. The presence of tumor suppressor genes in hybrid cells is indicated by loss of malignant properties, i.e., loss of in vitro characteristics of cancer cells, such as, density dependent inhibition of growth, growth in agar, stimulation of growth by autocrine secretion of growth factors and ability to form tumors in athymic nude mice.

21. Identification of Novel Genes

Including transforming genes in naturally occurring cancers, growth factor genes, oncogenes, tumor suppressor genes, using standard molecular biological techniques (Davis et al., Methods in Molecular Biology, New York: Elsevier, pp. 167–189, (1986)) and techniques such as cDNA substraction cloning and the like.

22. Model for Alternatives to Animal Testing

There is presently a great deal of concern about the use of animals for testing products for human use. With the upsurge of interest in the Animal Rights Movement, considerable emphasis is being placed on the development of cell culture models as alternatives to using animals for testing. The drug and the cosmetic industry and manufacturers of household and industrial chemicals are interested in using cell culture models, especially those derived from human cells, to test for human toxicity of their products.

A kit for screening carcinogenic or antineoplastic agents and for any other usage as described herein supra, is easily assembled, comprising the cell line(s) of the present invention. Other components routinely found in such kits may also be included with instructions for performing the test.

The cells of the present invention may be made malignant by exposure to a virus, transfected with an activated oncogene, radiation or to chemical carcinogens including, for example, N-methyl-N'-nitro-N-nitrosoguanidine (MNNG) or N-methyl-N-nitrosourea (NMU), tumor promoters such as and by promotion with 12-O-tetradecanoylephorbol-13-acetate (TPA) or hormones. All of this is well known to those skilled in the art.

The cell lines include cells of epithelial and fibroblast origin. The epithelial cells include stem, basal, intermediate and differentiated luminal cells. The prostatic cells can be from various donors and cell types.

An application which is co-pending with the present application by some of the inventors herein describes HPV immortalized cells. This invention is different than the present invention since a different virus was used.

It is intended that the foregoing description be only illustrative of the present invention and that the present invention be limited only by the hereinafter appended claims.

We claim:

1. An immortalized adult human normal prostatic epithelial or fibroblast cell derived cell line free of other cell lines and containing DNA of adenovirus and simian virus 40 as a hybrid virus, the cell line having the identifying characteristics of the prostatic epithelial or fibroblast cell without the hybrid virus in addition to being immortalized by the hybrid virus.

2. The cell line of claim 1 wherein the simian virus 40 is deposited as ATCC VR-239.

3. The cell line of claim 1 wherein the adenovirus is adenovirus 12 deposited as ATCC VR-863.

4. The cell line of claim 1 wherein the adenovirus is adenovirus 12 and the simian virus 40 is deposited as ATCC VR-863 and VR-239, respectively.

5. The cell line of claim 1 which produces prostate specific antigen.

6. A cell line deposited as ATCC CRL 11611.

7. An immortalized human prostatic epithelial cell line wherein the cell line has the phenotypic characteristics comprising: cytokeratins 8/18 positive, desmin negative, Factor VIII negative, contact inhibited, anchorage dependent, androgen responsive, plasminogen activator secretion normal, collagenase secretion normal, is non-tumorigenic, produces prostate specific antigen and contains a hybrid virus of adenovirus and simian virus 40.

8. The cell line of claim 7 wherein the simian virus 40 is deposited as ATCC VR-239 and the adenovirus is adenovirus 12 deposited as ATCC VR-863.

9. A kit for screening a carcinogenic, chemotherapeutic, chemopreventive, anti-invasive, anti-metastatic or anti-angiogenic agent comprising an immortalized adult human prostatic epithelial cell derived cell line containing DNA of adenovirus and simian virus 40 as a hybrid virus, the cell line having the identifying characteristics of the prostatic epithelial cell without the hybrid virus in addition to being immortalized by the hybrid virus.

10. The kit according to claim 9 wherein the immortalized cell line is immortalized using simian virus 40 deposited as ATCC VR-239 and adenovirus 12 deposited as ATCC VR-863.

11. The kit according to claim 9 wherein the immortalized cell line is non-tumorigenic.

12. The kit according to claim 9 wherein the immortalized cell line is made tumorigenic after additional transformation by infection with oncogenic viruses, activation of oncogenes, transfection with activated oncogenes, loss of suppressor genes, or chemical exposure or radiation.

13. The kit of claim 9 wherein the cell line produces prostate specific antigen.

14. A method for producing an immortalized adult human normal prostatic epithelial or fibroblast cell derived cell line which comprises:

(a) providing non-malignant human prostatic epithelial or fibroblast cells in a medium; and (b) infecting the human prostatic epithelial or fibroblast cells in the medium with DNA from adenovirus and simian virus 40 as a hybrid virus to thereby immortalize the cells with the hybrid virus to produce the cell line, wherein the cell line has the identifying characteristics of the prostatic epithelial or fibroblast cell without the hybrid virus in addition to being immortalized by the hybrid virus.

15. The method of claim 14 wherein the simian virus 40 is deposited as ATCC VR-239.

16. The method of claim 14 wherein the adenovirus is adenovirus 12 deposited as ATCC VR-863.

17. The method of claim 14 wherein the adenovirus is adenovirus 12 and the simian virus 40 is deposited as ATCC VR-863 and VR-239, respectively.

18. The method of claim 14 wherein the immortalized cell line deposited as ATCC CRL 11611.

19. The method of claim 14 wherein after the infecting in step (b) the cell line is subjected to multiple cloning to select a non-virus producing cell line in a serum free, chemically defined medium.

20. The method of claim 19 wherein the medium contains pituitary extract and epidermal growth factor.

21. The method of claim 14 wherein the cell line produces prostate specific antigen.

* * * * *

UNITED STATES PATENT AND TRADEMARK OFFICE
CERTIFICATE OF CORRECTION

PATENT NO. : 5,610,043
DATED : March 11, 1997
INVENTOR(S) : Mukta M. Webber and Johng S. Rhim It is certified that error appears in the above-indentified patent and that said Letters Patent is hereby corrected as shown below:

On title page, in item [73] Assignee should
include "Board of Trustees operating Michigan State University, East Lansing, Michigan"

Column 4, line 28, after "PWR-1E", --cells-- should be inserted.

Column 6, line 44, "ca/Mg-free" should be
--Ca/Mg-free--.

Column 7, line 22, "AD12-V40" should be --AD12-SV40--.

Signed and Sealed this

Seventeenth Day of June, 1997

Attest:

BRUCE LEHMAN

*Attesting Officer*    *Commissioner of Patents and Trademarks*